… … …

United States Patent [19]
Schubert et al.

[11] Patent Number: 5,949,082
[45] Date of Patent: Sep. 7, 1999

[54] CERAMIC RADIATION SOURCE ASSEMBLY WITH METALIZED SEAL FOR GAS SPECTROMETER

[75] Inventors: W. Peter Schubert, Thornton; G. Lamar Kirchhevel, Westminster, both of Colo.

[73] Assignee: Datex-Ohmeda, Inc., Tewksbury, Mass.

[21] Appl. No.: 09/046,051

[22] Filed: Mar. 23, 1998

[51] Int. Cl.⁶ .................................................. G01N 21/35
[52] U.S. Cl. .................. 250/493.1; 250/343; 250/495.1; 250/504 R
[58] Field of Search ............... 250/493.1, 494.1, 250/495.1, 504 R, 343, 346

[56] References Cited

U.S. PATENT DOCUMENTS

| | | | |
|---|---|---|---|
| 4,157,470 | 6/1979 | Kotaka et al. | 250/345 |
| 4,899,053 | 2/1990 | Lai et al. | 250/343 |
| 4,957,371 | 9/1990 | Pellicori et al. | 356/419 |
| 5,059,397 | 10/1991 | Melly et al. | 250/504 R |
| 5,092,342 | 3/1992 | Hattendorff et al. | 128/719 |
| 5,220,173 | 6/1993 | Kanstad | 250/493.1 |
| 5,260,574 | 11/1993 | Becker | 250/338.1 |
| 5,401,966 | 3/1995 | Gray et al. | 250/343 |
| 5,440,143 | 8/1995 | Carangelo et al. | 250/573 |
| 5,714,759 | 2/1998 | Nelson | 250/343 |
| 5,731,581 | 3/1998 | Fischer et al. | 250/339.13 |
| 5,731,583 | 3/1998 | Bailey et al. | 250/343 |

Primary Examiner—Kiet T. Nguyen
Attorney, Agent, or Firm—Holme Roberts & Owen LLP

[57] ABSTRACT

A radiation source assembly is provided that is particularly apt for use in an anesthetic gas monitoring device (e.g., a gas spectrometer) to enhance maintenance of initial calibration conditions therewithin. In one embodiment a respiratory gas spectrometer includes a containment assembly that defines an internal containment area(s) within which a ceramic radiation source, an optical assembly, a sample gas assembly, and a radiation detection assembly are positioned. The radiation source assembly is provided for positioning and supporting the ceramic radiation source relative to the optical assembly within an internal containment area of the gas monitor. The radiation source assembly provides for enhanced sealing between the ceramic radiation source and adjoining componentry. The radiation source assembly is selectively retractable from the containment assembly to permit periodic servicing (e.g., replacement of the radiation source) without requiring disassembly of the gas spectrometer.

24 Claims, 8 Drawing Sheets

CERAMIC RADIATION SOURCE ASSEMBLY WITH METALIZED SEAL FOR GAS SPECTROMETER

FIELD OF THE INVENTION

This invention relates to gas spectrometers for measuring the concentration of predefined components of a gas sample, and is particularly apt for use in respiratory gas spectrometers for measuring the concentration of oxygen, $CO_2$, and/or one or more anesthetic agents in a respiratory gas stream sample.

BACKGROUND OF THE INVENTION

Gas monitoring devices, such as gas spectrometers, are utilized in a wide variety of industrial and medical applications to monitor the presence and concentration of one or more predefined components in a gas sample. Typically, light of a known spectral content is directed through a gas sample and the intensity of the transmitted light at a number of different center-wavelengths is detected. By utilizing known light absorption characteristics of the predefined gas components at the center-wavelengths, the detected light intensities provide a basis to determine, via statistical processing, the concentrations of the predefined components. As will be appreciated, it is important that the initial calibration conditions of the spectrometer be maintained in order to accurately relate the measured light intensities to gas component concentrations.

This is particularly true in respiratory gas spectrometers used to measure the concentration of carbon dioxide and/or oxygen and one or more anesthetic agents, such as nitrous oxide, halothane, enflurane, isoflurane, sevoflurane and desflurane, in a respiratory gas stream. In such applications, a separate sample stream is typically drawn from the patient respiratory gas assembly and directed into a sample chamber that is positioned on the optical path between the light source and the detector. To maintain high accuracy, any significant absorbers of light at the center-wavelengths of interest that are on the optical pathway between the light source and detector should be accounted for during calibration and the related calibration conditions should be maintained during use.

Given such calibration considerations, the optical pathway(s) utilized in respiratory gas spectrometers may be disposed within a sealed housing. Because even a small variation in the concentration of absorbers of light, such as carbon dioxide, may require recalibration, it is important that the housing be adequately sealed from sources of gaseous contaminants. In this regard, it should be noted that, given the responsivity needs of respiratory gas spectrometers, it has been found desirable to utilize light sources operating at relatively high temperatures (e.g., temperatures exceeding 900° C.). In particular, such light sources may comprise one or more ceramic elements for actual radiation transmission. While such sources provide high responsivity they also generate a large amount of heat which can present challenges for maintaining a sealed environment.

More particularly, the present inventors have recognized that the use of a high temperature light source may affect the sealing of a gas spectrometer due to, for example, outgassing from or leakage through/around sealing components (e.g., gaskets, o-rings, sealing compounds, and the like) and leakage due to differing thermal expansion/contraction rates of adjoined components. Further, it has been recognized that excessive heat transfer from a high temperature light source may adversely impact the operation/calibration of electrical componentry used in a spectrometer, including in particular the radiation detectors employed therein.

SUMMARY OF THE INVENTION

In view of the foregoing, a primary objective of the present invention is to provide a gas spectrometer having a high degree of maintainable accuracy, and, more particularly, which is capable of maintaining initial calibration conditions to reliably achieve the desired accuracy. A related objective of the invention is to enhance the maintenance of sealed conditions within gas spectrometers, and in particular, a spectrometer that utilizes one or more ceramic radiation elements.

Another objective of the present invention is to provide a highly accurate and responsive gas spectrometer that utilizes one or more ceramic radiation elements and that is otherwise readily serviceable.

To achieve such objectives and realize other associated advantages, the present invention recognizes the desirability of providing an enhanced seal arrangement between a light source that includes a ceramic element(s) and adjoining structural support components of a gas spectrometer. Further, the present invention recognizes the importance of providing a retractable light source to facilitate selective servicing/replacement (e.g., of an assembly that includes the ceramic element(s)), while preserving the improved seal between the retractable light source and the containment assembly of the gas spectrometer.

In general, and while not limited to such applications, gas spectrometers that may realize the benefits of the present invention may include a containment assembly defining one or more closed, internal containment area(s), an infrared, ceramic radiation source, and an optical assembly positioned within the containment assembly to direct the infrared radiation on one or more pathways. A sample gas chamber may be provided on at least one optical pathway within the containment assembly for containing and cycling a respiratory gas sample therethrough. A detector assembly may be positioned within the containment assembly to receive the unabsorbed infrared radiation transmitted through the sample gas chamber. For respiratory gas applications, the ceramic radiation source can be provided to emit black body radiation, including radiation in the 7 to 10 micrometer wavelength range.

To achieve emission of radiation in the 7–10 micrometer wavelength range, the ceramic radiation source may comprise ceramic elements (e.g., of silicon nitride construction) and an electrical heater element in direct thermal contact with the ceramic element(s). The emitter surface(s) of the ceramic element(s) may be elongate to facilitate the illumination/detection at a plurality of center-wavelengths. For example, the detector assembly may include multiple filters or a linear variable filter. Additionally, the ceramic radiation source may provide for a relatively uniform radiation emission distribution along the longitudinal extent of the source. In this regard, a radiation source having a substantially planar emitter surface, and more preferably, having two, oppositely directed substantially planar emitter surfaces for illuminating two optical paths may be employed.

In this regard, the ceramic radiation source may have a rectangular cross-section to provide the desired oppositely facing, planar emitter surfaces. To heat the emitter surfaces, the resistance heater element may be sandwiched between two planar, ceramic layers (e.g., each side of the rectangle forming an emitter surface). The electrical heater element may take various forms (e.g., sheet, mesh, wire strands, and the like) and, preferably, is capable of concentrating heat generation (i.e. operating at temperatures ranging from about 900° C. to about 1200° C.) at one end of the elongate emitter surface(s) to better control emission of radiation used in gas sample analyses. For example, the element may comprise a single wire having a serpentine configuration located near one end of the elongate emitter surface(s) to concentrate heat generation and therefore, radiation emission.

As indicated, the radiation source may include exterior ceramic surfaces (e.g., the emitter surfaces), and may have a substantially rectangular cross-section. These characteristics raise sealing challenges. Such challenges include the lack of a metal-to-metal interface, differing rates of thermal expansion and contraction amongst mating components, and the sealing of a rectangular object (e.g., the absence of annular surfaces cross-section for employing conventional sealing methods). One method of sealing the radiation source is through the use of resilient sealing compounds (e.g., silicon rubber) and/or epoxies which creates a seal that may provide adequate sealing and structural strength for many gas spectrometer applications. However, resilient sealing compounds may be permeable to certain gases (e.g., $CO_2$), and epoxies may be subject to cracking if there is a significant difference in the rate of thermal expansion between the epoxies and the mated components. For example, the rate of thermal expansion of the exterior ceramic surface of the radiation source may differ from that of the adjoining metallic components by at least 20 percent and often by more than 30 percent.

To provide an improved seal and address the noted sealing challenges, the radiation source assembly comprising the present invention includes the ceramic radiation source, a metalized portion thereupon, a holder for positioning and supporting the radiation source within the containment assembly and a brazed interface layer between the metalized portion and holder. To provide a bonding interface on the ceramic radiation source, the metalized portion is positioned about the periphery of the radiation source at a location that facilitates interconnection with the holder. The metalized portion may comprise one or more metal components suitable for both bonding to the exterior ceramic surface of the radiation source and for brazed interconnection to the holder. For example, the metalized portion may comprise a copper-silver alloy which acceptably bonds to silicon nitride ceramic elements. The metalized portion may be bonded to the exterior ceramic surface of the radiation source by heating the metal utilized and radiation source to at least the melting point of the metal selected. This heating may be done under vacuum furnace or nitrogen furnace conditions to provide a substantially oxygen-free environment to enhance bonding. At this temperature and under these furnace conditions, the metal utilized for the metalized portion wets to the exterior ceramic surface to form a structurally strong and substantially gas impermeable seal between the metalized portion and the radiation source. As will be appreciated, the metalized portion may be bonded to the exterior ceramic surface through other appropriate metalizing operations, such as metal spraying or vacuum deposition.

Of importance, the bonding of a metallic interface (i.e., the metalized portion) onto the exterior ceramic surface of the radiation source facilitates interconnection of the radiation source to the holder used to supportably position the radiation source within the containment assembly of the gas spectrometer. In this regard, the holder preferably includes an opening for receiving the radiation source therein, e.g., a rectangular bore for receiving the rectangularly cross-sectioned radiation source. In this regard, the elongate radiation source is disposed within the holder so as to at least partially align the metalized portion with the inner surfaces of the holder. The holder may have various external configurations to provide suitable mating surfaces between the holder and the containment assembly. For example, the holder may have at least one circular cross-section to provide a surface for conventional sealing (e.g., an o-ring, resilient gasket, and the like).

To achieve a substantially gas impermeable interface or seal between the metalized portion of the source and the holder, the bonding of the holder to the metalized portion may be completed employing a brazing process. The brazing filler metal selected for this brazing operation should therefore bond to both the holder and the metalized portion to form a brazed interface layer between these two components. As can be appreciated, the brazed interface layer provides structural support of the radiation source, through the metalized portion, within the holder. The brazed interface layer and the corresponding metallic bonds create a very effective seal against gaseous contaminants. As will be apparent, it is preferable for the brazing filler metal selected to have a melting point i) that is lower than the melting point of the metalized portion to facilitate brazing, and ii) that is higher than the operating temperature at the interface between the holder and the radiation source. For example, the braze interface layer may comprise silver or tin-lead filler metals each of which has a suitable melting point and bonding characteristics.

The holder is preferably fabricated from a metal alloy suitable for brazing operations. Further the holder should be selected to have a coefficient of thermal expansion that is compatible with the exterior ceramic surface on the source so as to reduce any stress on the brazed bonds therebetween during operation of the gas spectrometer. For example, the holder may be fabricated from a metal alloy (e.g., Zirconium Metal 702 or Kovar) having a coefficient of thermal expansion of less than about $5.0\ \mu in/in\cdot°$ F. Nitrogen or hydrogen brazing the source and holder may be advantageously performed at substantially atmospheric pressure when the holder is fabricated from Kovar. Alternatively, vacuum brazing may be employed with metal alloys (e.g., Zirconium 702) containing hard-to-dissociate oxides. As can be appreciated, the combination of the above noted seals and bonding layers creates an improved seal between the radiation source and the holder which facilitates the maintenance of the calibration conditions within the gas spectrometer.

As indicated, radiation sources employable in the present invention may operate at relatively high temperatures and generate substantial heat, including excess heat that is not used in sample gas analyses. To facilitate the transfer of the excess heat to the exterior environment, the gas spectrometer may include a heat transfer assembly that acts as a heat sink via positioning at a portion within the containment assembly of the gas spectrometer and positioning of a portion exterior to the containment assembly. The radiation source assembly may be disposed within the heat transfer assembly so that heat emitted by the radiation source is, primarily, either directed toward the optical assembly for gas sample analyses or absorbed by the internally positioned portion of the heat transfer assembly and conducted to the exterior environment via the externally positioned portion. In this regard, the heat transfer assembly may include a substantially cylindrical chamber for housing the elongate radiation source. To facilitate a sealed connection with the containment assembly of the gas spectrometer, the heat transfer assembly may include a radially extending flange that is positioned in face-to-face relation with the outside surface of an outer wall of the containment assembly and that is directly connected or integral with the chamber and externally positioned portion of the heat transfer assembly may include a number of laterally extending fins that are interconnected to the chamber and/or the flange so as to provide a thermally conductive pathway from the chamber and/or flange to the exterior environment and to provide convective heat transfer surfaces (i.e., the fin surfaces) to release the excess heat.

The present invention further provides for the servicing and replacing of finite-lived radiation sources. In this regard, the invention provides for selective servicing of the radiation source assembly free from disassembly of the gas spectrometer, and for sealably interconnecting the radiation source assembly with the heat transfer assembly to maintain calibration conditions within the gas spectrometer during operation. Specifically, the holder of the radiation source assembly may include a first cylindrical portion that facilitates positioning the holder within the chamber of the heat transfer assembly. For example, the outer diameter of the first cylindrical portion of the holder may be selected to be slightly smaller than the inner diameter of the chamber member to nearly create a press fit. The holder may further include a second cylindrical portion. The outer diameter of the second portion of the holder is larger than both the outer diameter of the first cylindrical portion (e.g., so as to define a step therebetween) and the inner diameter of the chamber (e.g., so as to control the insertion depth of the radiation source within the chamber to a predetermined distance). The step between the first and second portions allows for the positioning of a resilient sealing member (e.g., an o-ring) between the holder and step of the heat transfer assembly. As such, the holder can be selectively removed from and reinserted into the heat transfer assembly for source servicing. To further facilitate selective removal/interconnection of the radiation source assembly relative to the heat transfer assembly, the second portion of the holder may be configured to provide connective interfaces (e.g., holes, recesses for the heads of screws, and the like) with mechanical fasteners (e.g., screws) that may be disposed in threaded holes in the flange of the heat transfer assembly.

Numerous additional aspects and advantages of the present invention will be apparent upon consideration of the further description that follows.

DETAILED DESCRIPTION

Figure 1A:
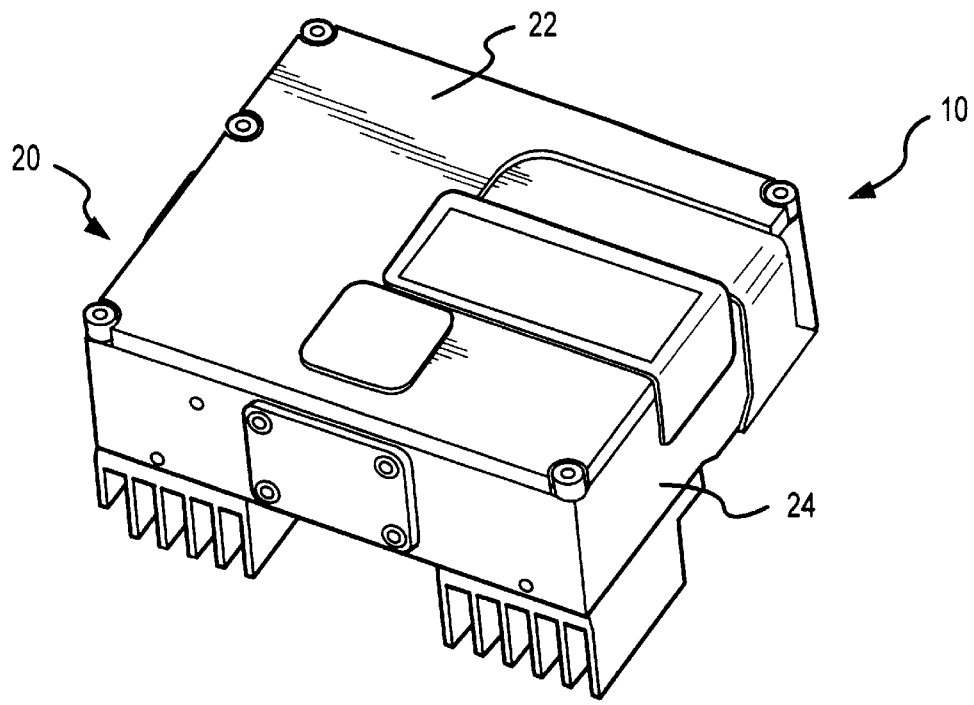
FIG. 1A illustrates a perspective top view of an anesthetic gas monitoring device.
Figure 1B:
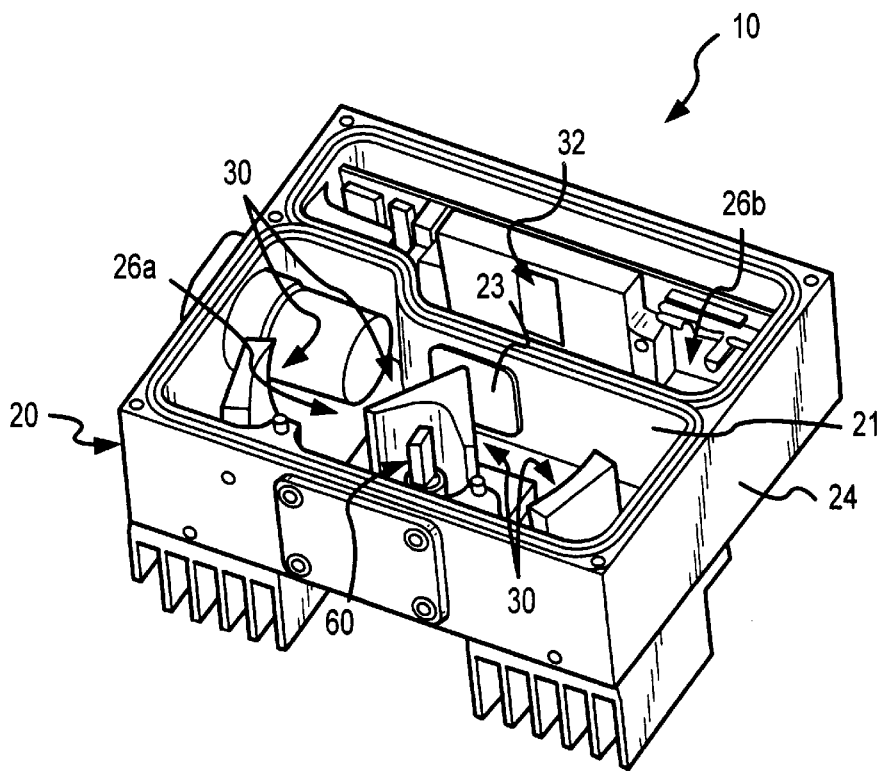
FIG. 1B illustrates a perspective top view of the anesthetic gas monitoring device of FIG. 1A with a top member of a containment assembly removed.

FIGS. 1A–7D pertain to an embodiment of a radiation source assembly 60 of the present invention for use in an anesthetic gas monitoring device 10. The anesthetic gas monitoring device 10 includes a containment assembly 20 that may be principally defined by a top member 22 and a bottom member 24, which may be sealably assembled together (e.g., by use of a resilient, continuous gasket and screws disposed in threaded holes). FIG. 1B illustrates a top view of the anesthetic gas monitoring device 10 with the top member 22 of the containment assembly 20 removed to show the positioning of the radiation source assembly 60 within the containment assembly 20.

Figure 2:
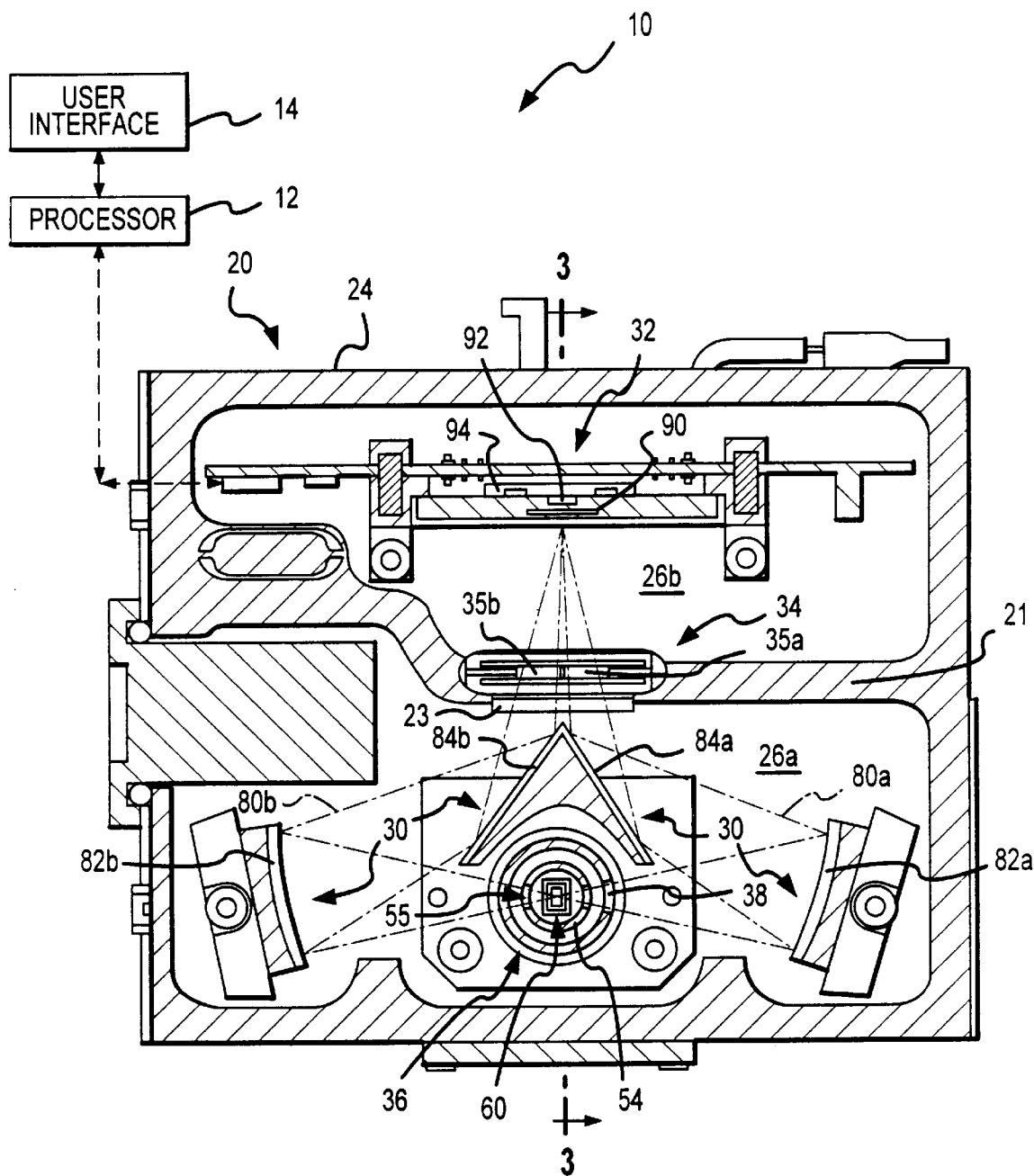
FIG. 2 is a top cross-sectional view of the anesthetic gas monitoring device of FIGS. 1A and 1B.
Figure 3:
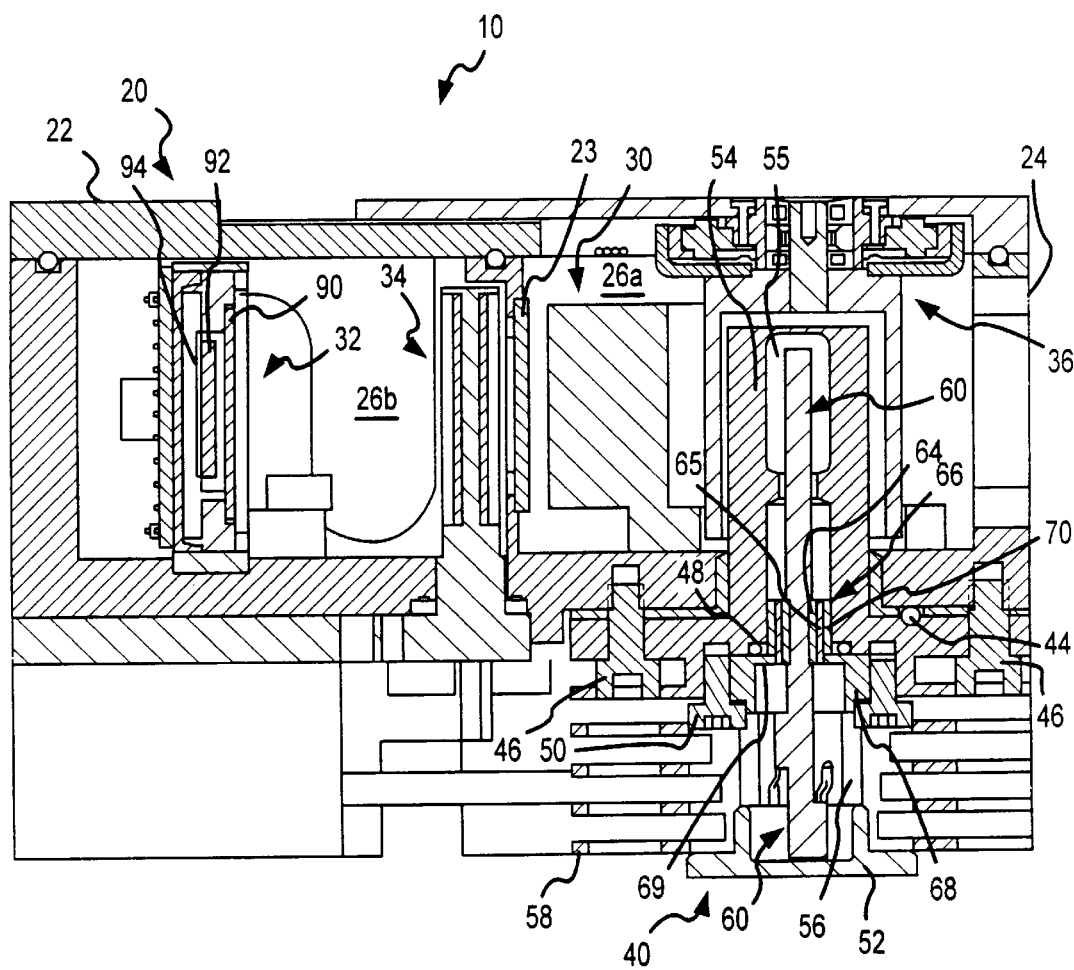
FIG. 3 is a cross-sectional view of the embodiment shown in FIG. 2 taken at line 3—3.

As shown in FIGS. 2 and 3, the containment assembly 20 defines a primary, enclosed, internal containment area 26a and a secondary, enclosed, internal containment area 26b. The radiation source assembly 60, a heat transfer assembly 40, an optical assembly 30, and a chopper assembly 36 are all at least partially disposed within the primary containment area 26a. A detector assembly 32 and a gas sampling assembly 34 are each at least partially disposed within the secondary containment area 26b. The noted components cooperate to provide for accurate monitoring of a concentration of preselected components within a respiratory gas stream cycled through gas sampling assembly 34. In this regard, the present invention may be readily utilized in a respiratory gas spectrometer as disclosed in U.S. patent application Ser. No. 08/403,161, hereby incorporated by reference in its entirety.

During operation of the anesthetic gas monitoring device 10, a source element 61 of the radiation source assembly 60 may operate at a maximum temperature from up to about 900° to about 1200° C. to emit radiation across at least a 4–12 micron wavelength range. The chopper assembly 36 includes a window 38 and is rotatable about source element 61 for alternatively transmitting radiation on first and second optical paths 80a and 80b (as defined by optical assembly 30).

In the later regard, the optical assembly 30 includes first and second spherical mirrors 82a and 82b for collecting and directing radiation from source element 61 on first and second optical paths 80a and 80b. The resultant, converging optical beams on paths 80a and 80b are separately redirected via first and second flat mirrors 84a and 84b, respectively, through gas sampling assembly 34.

Referring to FIG. 2, the containment assembly 20 includes an internal wall 21 defining the separate internal containment areas 26a and 26b. Internal wall 21 is provided with an opening therethrough so as to receive gas sampling assembly 34 and transparent window member 23. Both window member 23 and gas sampling assembly 34 are positioned on optical paths 80a, 80b. The gas sampling assembly 34 includes a gas sample chamber 35a and a reference gas chamber 35b disposed relative to optical assembly 30 such that the first converging beam on path 80a passes through opposing, transparent windows of the gas sample chamber 35a, and the second converging beam on path 80b passes through opposing, transparent windows of the reference gas chamber 35b. The gas sample assembly 34 is interconnected to gas flow lines (not shown) for continuously cycling a sample stream of respiratory gas from a patient through the gas sample chamber 35a.

Referring to FIGS. 2 and 3, the detector assembly 32 includes an upstanding linear variable filter 92, an adjacent band pass filter 90, and an upstanding linear array of pyro-electric detector elements 94 positioned behind the linear variable filter 92 and the band pass filter 90. The detector assembly 32 is positioned so that non-absorbed radiation transmitted through the gas sample chamber 35a and the reference gas chamber 35b on paths 80a and 80b, respectively, is filtered by the linear variable filter 92 and the band pass filter 90 and then detected by the linear detector array 94. As will be appreciated, the detected radiation will not include radiation that is absorbed by gas component(s) present along paths 80a and 80b, including, in particular, gas component(s) contained within sample gas chamber 35a.

In operation, the linear variable filter 92 will simultaneously filter transmitted radiation in a spatially distributed manner across a wavelength range, including the 7–10 micron range. The 7–10 micron range covers sub-ranges across which many anesthetic gas agents will display unique radiation absorbance characteristics. The band pass filter 90 will pass unabsorbed radiation in the 4–5 micron range which encompasses the range within which $CO_2$ displays unique radiation absorbance characteristics. By utilizing linear detector array 94 to simultaneously obtain intensity measurement values at predetermined center-wavelengths across the 7–10 and 4–5 micron wavelength ranges, the resultant data can be provided to processor 12 for multivariate statistical processing and determination of the concentration of one or more anesthetic gas agents and $CO_2$ for visual or audible output/alarm by user interface 14.

Referring to FIGS. 4–7D, the radiation source assembly 60 of the present invention includes the source element 61, a metalized portion 64, a brazed interface layer 65, and a holder 66. The elongated, infrared radiation source element 61 transmits radiation to the optical assembly 30 during operation of the anesthetic gas monitoring device 10. As illustrated in FIG. 5C, the source element 61 has a rectangular cross-section, including substantially planar surfaces for emitting radiation in opposite directions simultaneously. As can be appreciated, a planar surface provides a more intense and even (e.g., less diffracted) source of illumination. The source element 61 includes an interior heater element 63 substantially enclosed within an exterior ceramic layer 62. As can be appreciated, the interior heater element 63 can be any suitable electrical element (e.g, sheet(s), wire(s), screen(s), or a combination thereof) capable of causing the opposing, planar surfaces of ceramic layer 62 to radiate at temperatures from up to about 900° C. to about 1200° C. For example, the interior heater element 63 may comprise a single resistance wire configured to have a serpentine configuration at a predetermined position along the source element 61 for enhancing heat generation (e.g., concentrating heat generation) proximal to the slots 55, shown in FIGS. 3 and 4, of the chamber member 54.

The illustrated exterior ceramic layer 62 may be constructed from a substantially homogeneous black silicon nitride compound. The elongate, homogeneous exterior ceramic layer 62 allows complete, substantially even, and intense illumination to be provided to the optical assembly 30 and the detector assembly 32 for enhanced polychromatic analysis of sample gases. To obtain a desirable intensity of light for accurately analyzing sample gases, the source element 61 is preferably operable at a maximum temperature greater than about 900° C. with the exterior ceramic layer 62 emitting black body radiation, specifically including radiation in the 7 to 10 micrometer wavelength region, at this temperature. During operation of the anesthetic gas monitoring device 10, the illustrated source element 61 reaches temperatures ranging from up to at least about 900° C. to about 1200° C.

To facilitate sealable positioning of the source element 61 within the internal containment area 26a, the metalized portion 64 of radiation source assembly 60 is bonded to the exterior ceramic layer 62 of the source element 61. The metalized portion 64 provides a continuous metallic interface on all sides of, and for at least a portion of the length of, the elongated source element 61. In this regard, the metalized portion 64 facilitates sealably interconnecting, through the use of the brazed interface layer 65, the rectangularly-shaped source element 61 to the metallic holder 66 which is concentrically disposed about the metalized portion 64. As will be appreciated, the inclusion of the metalized portion 64 and the brazed interface layer 65 improves the gas seal that is achievable and maintainable between the holder 66 and the source element 61.

As illustrated in FIGS. 3–7D, the holder 66 includes first cylindrical portion 70 and a larger second cylindrical portion 68, such portions being adjoined by a smooth, planar step surface 69. Step surface 69 facilitates sealable assembly of the radiation source assembly 60 within the heat transfer assembly 40 (e.g., by using o-ring 48 and screws 50). This arrangement also advantageously facilitates selective servicing (e.g., replacing depleted source elements 61) of the radiation source assembly 60 free from disassembly of the containment assembly 20. Second cylindrical portion 68 is a circular cross-section which facilitates fabrication (e.g., machining) and disposition of the holder 66 within the heat transfer assembly 40. The holder 66 is at least partially hollow with a rectangular bore located on a central longitudinal axis of the holder 66 to enhance positioning of the source element 61 within the holder 66. The holder 66 may be fabricated from various materials, and preferably metal alloys, that provide structural strength at the operating temperatures of the anesthetic gas monitoring device 10 and that facilitate accurate fabrication.

The described embodiment provides a durable, substantially gas impermeable seal between the source element 61 and the holder 66 via selection of materials having compatible thermal expansion rates. In this regard, the illustrated silicon nitride exterior ceramic layer 62 of the source element 61 has a thermal coefficient of expansion of about 2.0 $\mu$in/in•° F. The holder 66 may be fabricated from various metals (e.g., Zirconium Metal 702 or Kovar).

Referring to FIGS. 6A to 7D, a production method for one embodiment of the radiation source assembly 60 will now be discussed. Initially, the source element 61 is selected and, as illustrated, includes the exterior ceramic layer 62 for emitting radiation when heated during operation of the anesthetic gas monitoring device 10. The metalized portion 64 is then positioned about the periphery of the source element 61 at a location that facilitates interconnection with the holder 66 (to be discussed below) and bonded to the exterior ceramic layer 62. To provide a metallic interface on the source element 61 for metal-to-metal bonding with the holder 66, the metalized portion 64 may be fabricated from a material group consisting of brazing filler metals (e.g. copper-silver alloy) that also provide suitable characteristics for bonding to ceramic materials such as silicon nitride. The bonding of the metalized portion 64 to the source element 61 may be completed by at least temporarily heating the metal for metalized portion 64 and the source element 61 to a temperature above the melting point of the metal and below the melting point of the exterior ceramic layer 62 of the source element 61 and then cooling the components after the metalized portion 64 has wetted (e.g., bonded) to the exterior ceramic layer 62. This bonding may be done in a vacuum furnace or under nitrogen furnace conditions to provide a substantially oxygen-free environment during bonding. Alternatively, the bonding may be completed through a metal spraying process. The bond formed in each of these embodiments provides a continuous seal around the rectangularly shaped source element 61 to protect against gaseous contaminants, particularly $CO_2$.

Next, the source element 61, with the now interconnected metalized portion 64, is positioned within the holder 66. The metalized portion 64 is aligned with the inner surface of the first cylindrical portion 70 of the holder 66 to provide a mating surface for bonding the holder 66 to the metalized portion 64. To facilitate bonding by brazing, at least the first cylindrical portion 70 of the holder 66 may be fabricated from a material group consisting of metals that are suitable for brazing processes. As can be appreciated, the metal chosen for the holder 66 preferably has a coefficient of thermal expansion that is compatible to the coefficient of thermal expansion of the exterior ceramic layer 62. In this regard, the coefficient of thermal expansion for the metal alloy used to fabricate the holder 66 preferably is less than 5.0 $\mu$in/in•° F. Additionally, the oxidation properties of the metal chosen for the holder 66 may significantly affect brazing operations. For example, when the holder 66 is fabricated from Zirconium Metal 702, brazing may be performed at vacuum pressure to control oxidation and form a seal that is substantially gas impermeable and has sufficient structural strength. Alternatively, when the holder 66 is fabricated from Kovar brazing may be completed at atmospheric conditions with a nitrogen or hydrogen atmosphere.

In both brazing examples discussed, the brazing filler metal used in the bonding process forms the brazed interface layer 65 between the holder 66 and the metalized portion 64. The brazed interface layer 65 provides an effective seal against gas contaminants and structurally supports the source element 61 within the radiation source assembly 60. As can be appreciated, various brazing filler metals (e.g., silver, tin-lead, or gold-copper) may be selected for this bonding process. As indicated, the selection depends at least partially upon the respective coefficients of thermal expansion of holder 66 and metalized portion 64 and melting points of these components. In the later regard, the brazing filler metal selected should have a melting point below the melting point of the metalized portion 64. Additionally, to enhance the seal achieved in this bonding process, the clearance between the first cylindrical portion 70 of the holder 66 and the metalized portion 64 should be determined based on the expansion rates of these components and on the desirability of maintaining an adequate capillary action during brazing.

To improve the thermal environment within the containment assembly 20 while maintaining a sealed environment, the anesthetic gas monitoring device 10 includes heat transfer assembly 40 which is positioned at least partially exterior to the containment assembly 20 to provide an external convective heat transfer surface. The heat transfer assembly 40 includes a flange 42 to provide sealable, face-to-face contact with the bottom member 24 of containment assembly 20. The seal obtained is improved by use of a continuous, resilient sealing member 44 (e.g., an o-ring) and at least two connecting members 46 (e.g., screws). In this regard, the heat transfer assembly 40 is selectively retractable to facilitate servicing while enhancing maintenance of the calibration conditions within the containment assembly 20 during operation of the anesthetic gas monitoring device 10.

Figure 4:
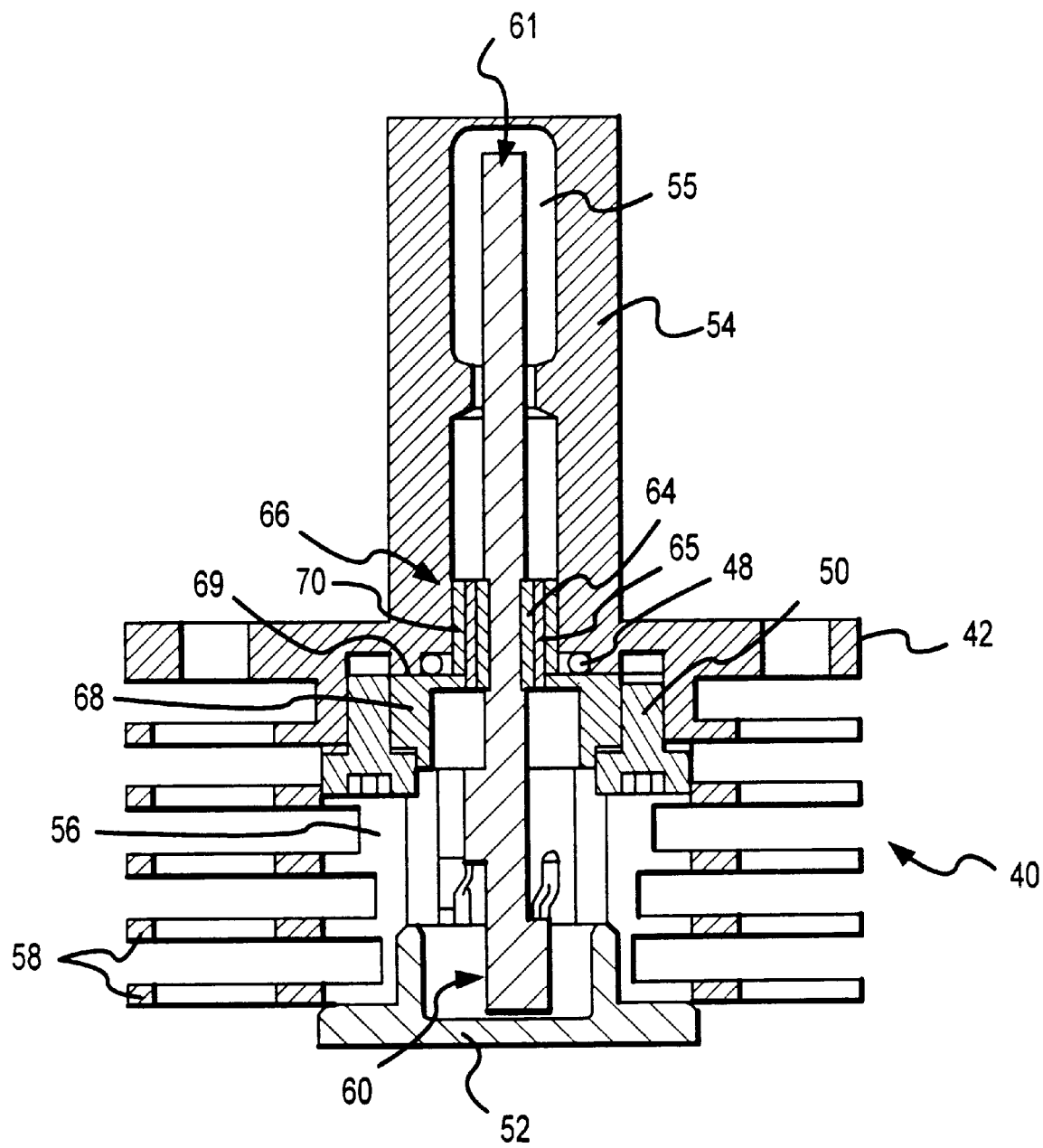
FIG. 4 is a cross-sectional view of the radiation source assembly illustrated in FIG. 3, shown in combination with other components of the anesthetic gas monitoring device.
Figure 5C:
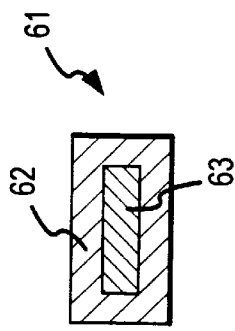
FIG. 5C is a cross-sectional view of the source element illustrated in FIG. 5B taken at line 5C—5C.
Figure 5B:
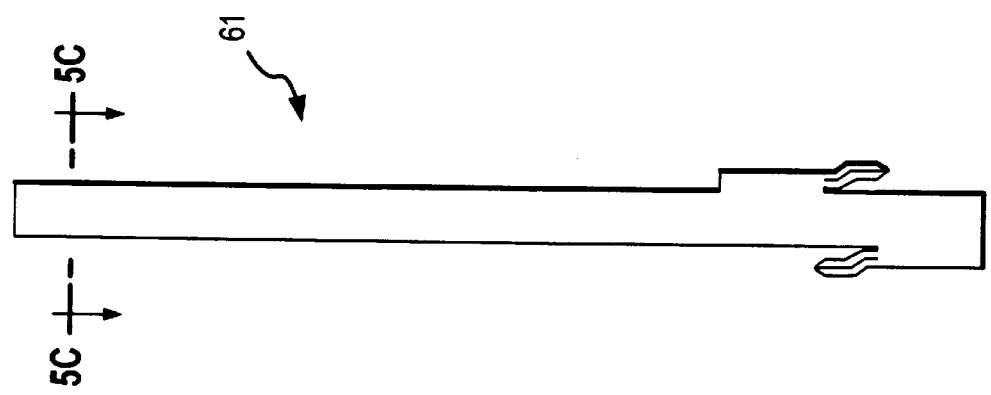
FIG. 5B is a front view of the source element illustrated in FIG. 5A.
Figure 5A:
FIG. 5A is a side view of an embodiment of a source element of the present invention.
Figure 6A:
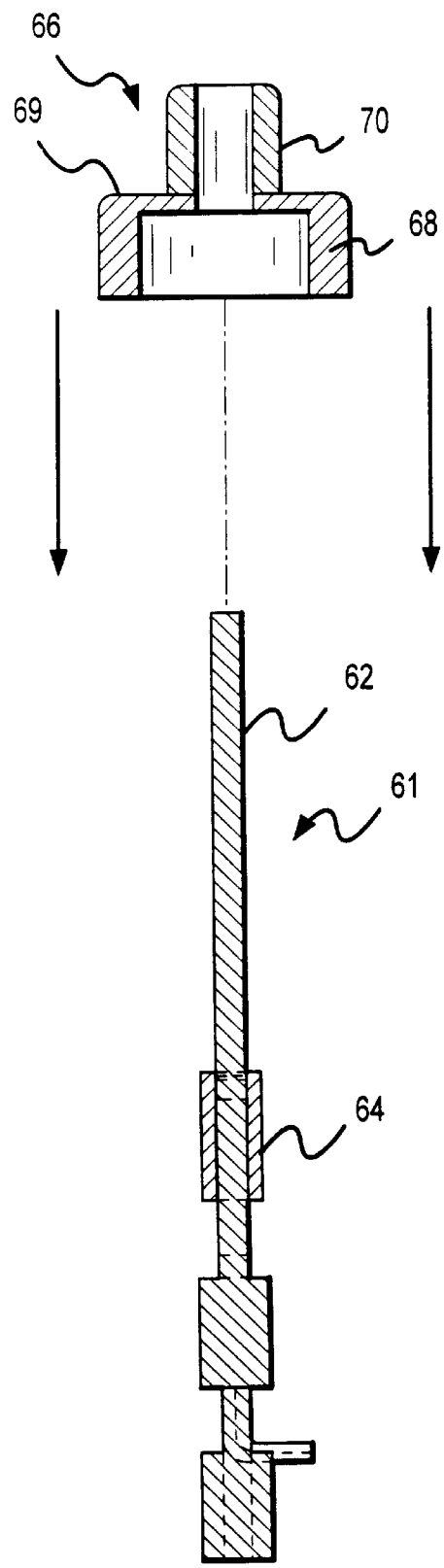
FIG. 6A is a partial exploded, cross-sectional side view of the radiation source assembly of the present invention.
Figure 6B:
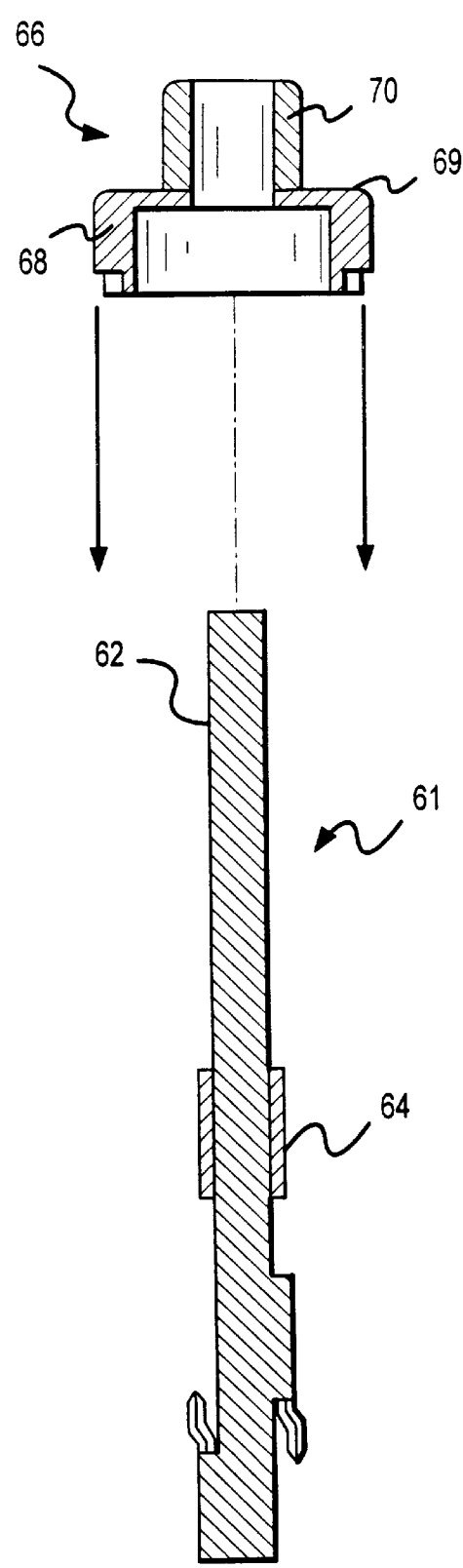
FIG. 6B is a partial exploded, cross-sectional front view of the radiation source assembly illustrated in FIG. 6A.
Figure 7A:
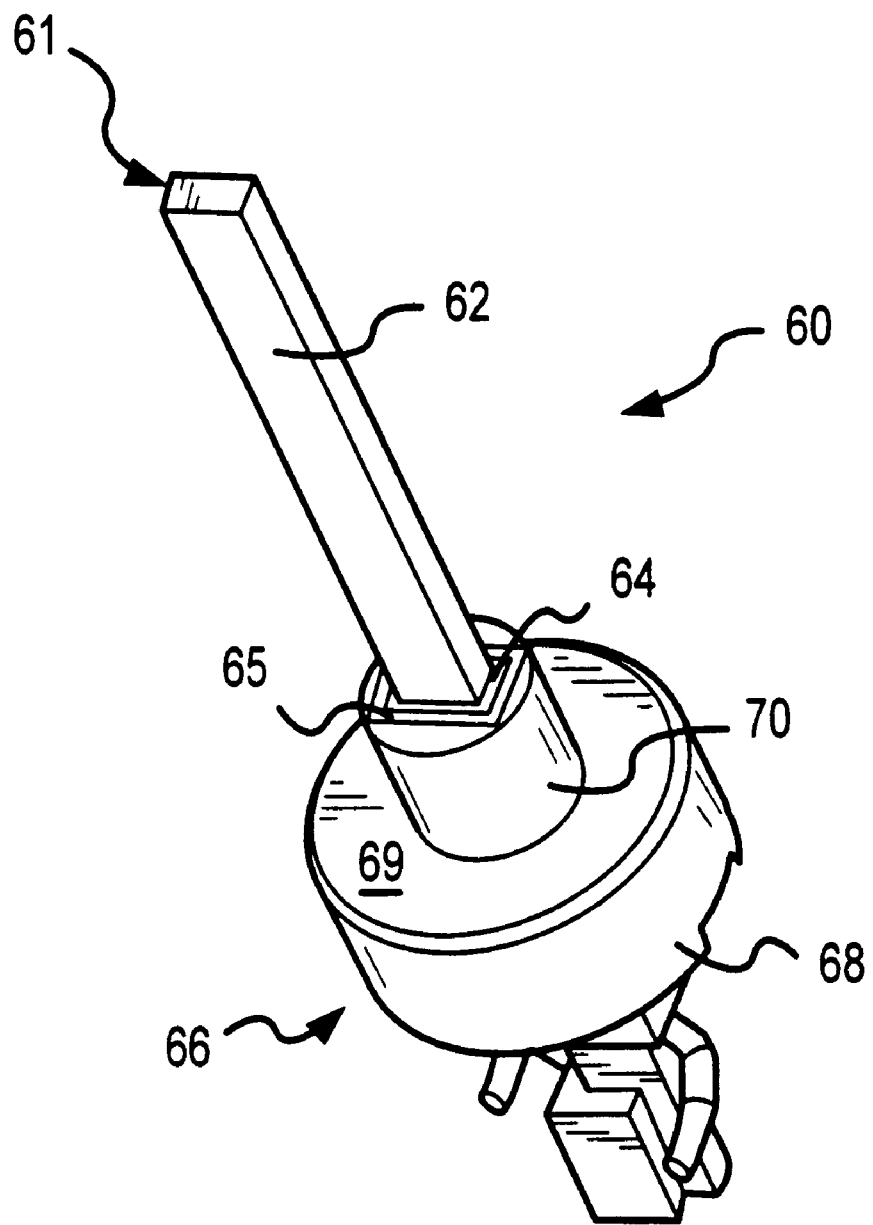
FIG. 7A is a perspective view of the radiation source assembly of the present invention.
Figure 7B:
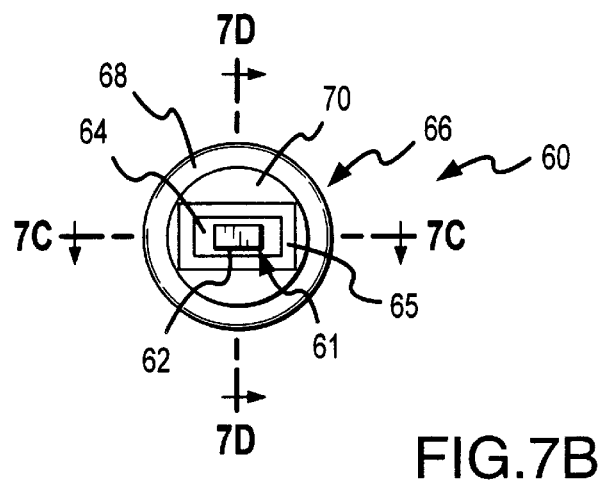
FIG. 7B is top view of the radiation source assembly illustrated in FIG. 7A.
Figure 7D:
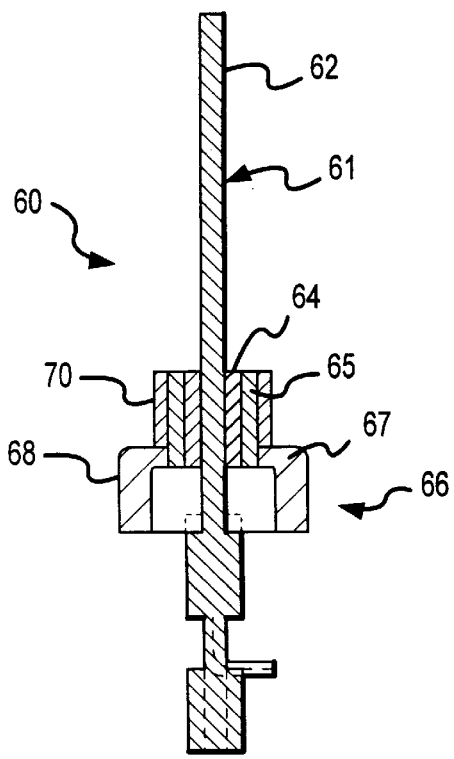
FIG. 7D is a cross-sectional view of the radiation source assembly illustrated in FIG. 7B taken at line 7D—7D.
Figure 7C:
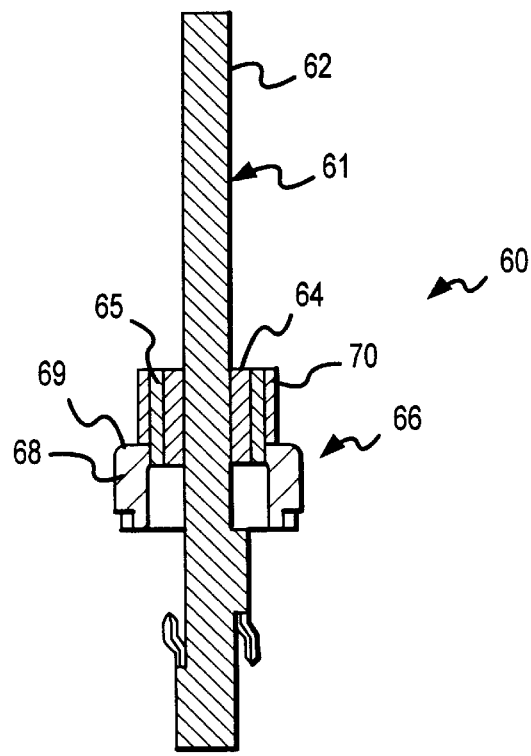
FIG. 7C is a cross-sectional view of the radiation source assembly illustrated in FIG. 7B taken at line 7C—7C.

As shown in FIG. 4, the radiation source assembly 60 is substantially, centrally disposed within a chamber member 54 of the heat transfer assembly 40. As can be appreciated, it is also desirable that the radiation source assembly 60 be selectively retractable from the heat transfer assembly 40 to facilitate replacement of the finite-lived source element 61. In this regard, the present invention facilitates obtaining a seal between the radiation source assembly and the chamber member 54 of the heat transfer assembly 40 by use of a continuous, resilient sealing member 48 (e.g., an o-ring) and at least two connecting members 50 (e.g., screws). The resilient sealing member 48 is concentrically disposed about first cylindrical portion 70 of holder 66 which facilitates proper positioning and on the smooth (e.g., machined to suitable surface finish), planar surface 69 of the second cylindrical portion 68 of the holder 66 which facilitates sealing between the resilient sealing member 48 and the holder 66. To physically seal the heat transfer assembly 40 and thereby, protectively cover the radiation source assembly 60, the heat transfer assembly 40 further includes a cover 52 that may be interconnected (e.g. by a threaded or a press-fit connection allowing ready engagement and disengagement with the flange 42.

As can be appreciated, the continued accuracy of the anesthetic gas monitoring, device 10 during operation depends in part upon maintenance of the predetermined calibration conditions within the primary enclosed internal containment area 26a. In this regard, the second portion 68 of holder 66 has a circular cross-section and planar surface 69 for use in sealing. As discussed above, planar surface 69 facilitates radiation source assembly 60 being assembled with the flange 42 of the heat transfer assembly 40 by use of resilient sealing member 48 and connecting members 50 (e.g., with the use of a wrench tool). Similarly, in this regard, an enhanced seal against gaseous contaminants is created between the metallic holder 66 and the rectangularly cross-sectioned source element 61 by bonding the metalized portion 64 to the exterior ceramic layer 62 of the source element 61. A second seal is obtained in the radiation source assembly by forming a brazed interface between the metallic holder 66 and the metalized portion 64 through a brazing process. These seals each significantly reduce the amount of gaseous contaminants, such as $CO_2$, entering the primary enclosed internal containment area 26a from sources exterior to the anesthetic gas monitoring device 10. In this manner, the radiation source assembly 60 allows the source element 61 to be readily replaced/serviced while providing for excellent sealing of the containment assembly 20 even during high temperature operations, thus maintaining the calibration and accuracy of the anesthetic gas monitoring device 10.

To further maintain accurate, reliable operation of the anesthetic gas monitoring device, the heat transfer assembly 40 absorbs excess heat (e.g., heat not used in sample gas analysis) and conducts the absorbed heat to the exterior of the containment assembly 20. The concentrically disposed chamber member 54 of heat transfer assembly 40 includes two slots 55 for directing and concentrating the radiation emitted from the radiation source assembly 60. Excess radiation (e.g., radiation that does not pass through slots 55) is absorbed by the chamber member 54 and conducted to a thermally interconnected fin support member 56 of the heat transfer assembly 40. From the fin support member 56, the excess heat is conducted to fins 58 of the heat transfer assembly 40 which are disposed exterior to the containment assembly 20.

To improve the efficiency of the heat transfer, the heat transfer assembly 40 includes laterally extending fins 58 having a substantially circular cross-section for enhancing the amount of exposed surface area of the heat transfer assembly 40. As can be appreciated, the number, size, and shape of the fins 58 may be varied to achieve a desired heat transfer rate from the containment assembly 20. The size of the cross-sectional area of the fin support member 56 reduces the heat transfer area of the fins 58 since the fins 58 have a constant outer diameter to facilitate positioning of the heat transfer assembly 40 on the exterior of the containment assembly 20. To increase the heat transfer area of the fins 58, the cross-sectional area of the fin support member 56 may be decreased. As illustrated, the decrease in cross-sectional area of the support member 56 is a stepwise reduction at each fin 58 located more distally to the chamber member 54. In this manner, the cross-sectional area of the fin support member 56 is at its largest proximal to chamber member 54 to facilitate rapid conductive heat transfer away from the radiation source assembly 60 to the heat transfer assembly 40 while the heat transfer area of the fins 58 is larger in fins 58 positioned distally to chamber member 54. In this manner, the conductive and convective heat transfer rates are enhanced to improve the efficiency of heat transfer to the exterior environment. Additionally, as will be appreciated, the convective heat transfer rate may be improved by increasing air velocity (e.g., forced-air cooling) across the fins 58.

Numerous additional embodiments and variations of the invention will be apparent to those skilled in the art and are intended to be within the scope of the present invention, as defined by the following claims.

What is claimed is:

1. A method for making a radiation source assembly having enhanced sealed interfaces for use in an anesthetic gas monitoring device having a sealed environment, said method comprising the steps of:

selecting a source element for use within the anesthetic gas monitoring device for providing radiation to a detector assembly positioned within said sealed environment, said source element including an exterior ceramic layer for emitting radiation when heated to a predetermined temperature and an interior heater element disposed at least partially within said exterior ceramic layer for heating at least a portion of said exterior ceramic layer to said predetermined temperature;

first positioning a metalized portion about the exterior of said source element, said metalized portion comprising a metallic material for providing a metallic interface on said exterior ceramic layer of said source element;

first bonding said metalized portion to said source element to provide a continuous seal against gaseous contaminants along an interface between said source element and said metalized portion;

selecting a holder for providing structural support of said source and for providing a sealing surface with the anesthetic gas monitoring device;

second positioning said source element within said holder, said positioning including positioning at least a portion of said metalized portion adjacent to at least a portion of said holder; and second bonding said holder to said metalized portion, said second bonding forming a seal against gaseous contaminants between said holder and said metalized portion.

2. A method as recited in claim 1, said source element being elongate with a substantially rectangular cross-section for providing at least two oppositely-facing substantially planar radiation emitter surfaces.

3. A method as recited in claim 2, wherein said exterior ceramic layer substantially comprises a silicon nitride compound.

4. A method as recited in claim 3, wherein said metalized portion comprises silver-copper brazing filler metal.

5. A method as recited in claim 4, wherein said first bonding step comprises temporarily heating each of said metalized portion and said source element to a temperature above the melting point of the metalized portion and below the melting point of said source element under vacuum furnace conditions.

6. A method as recited in claim 4, wherein said first bonding step comprises temporarily heating said metalized portion and said source element to a temperature above the melting point of the metalized portion and below the melting point of said source element under nitrogen furnace conditions for providing a substantially oxygen-free environment during said first bonding.

7. A method as recited in claim 4, wherein said first positioning and said first bonding steps comprise a metal spraying operation.

8. A method as recited in claim 4, wherein said holder is fabricated from a material having a predetermined coefficient of thermal expansion of less than about $5.0 \,\mu in/in\cdot°$ F., wherein said second bonding step comprises a brazing operation performed at substantially atmospheric pressure using brazing filler metal selected from the group consisting of tin-lead solder alloy and silver-copper brazing filler metal.

9. A method as recited in claim 8, wherein said holder is fabricated from Kovar.

10. A method as recited in claim 4, wherein said holder is fabricated from a material having a predetermined coefficient of thermal expansion of less than about $5.0 \,\mu in/in\cdot°$ F., wherein said second bonding step comprises a brazing operation performed at vacuum pressure using brazing filler metal selected from the group consisting of tin-lead solder alloy, silver-copper brazing filler metal, and gold-copper brazing filler metal.

11. A method as recited in claim 10, wherein said holder is fabricated from Zirconium Metal 702.

12. A method as recited in claim 1, said holder having a substantially circular cross-section for providing a surface for mechanically and sealably interconnecting said radiation source assembly with the anesthetic gas monitoring device.

13. A radiation source assembly for use in a anesthetic gas monitoring device having a sealed environment, said radiation source assembly being positioned at least partially within said sealed environment, comprising:

a source element for providing radiation to a detector assembly positioned within said sealed environment;

a metalized portion laterally disposed about said source for providing a metallic interface on said source, said metalized portion being sealably bonded to said source to provide a continuous seal along an interface between said source and said metalized portion; and a holder laterally disposed about said metalized portion for physically supporting said metalized portion and said source within said radiation source assembly, said holder being interconnected to said metalized portion by a brazed interface layer to provide a continuous seal along an interface between said metalized portion and said holder.

14. A radiation source assembly, as recited in claim 13, wherein said source element includes an exterior ceramic layer for emitting radiation when heated to a predetermined temperature and an interior heater element disposed at least partially within said exterior ceramic layer for heating at least a portion of said exterior ceramic layer to said predetermined temperature.

15. A radiation source assembly, as recited in claim 14, wherein said exterior ceramic layer substantially comprises a silicon nitride compound.

16. A radiation source assembly, as recited in claim 14, said source element having a rectangular cross-section for providing at least two oppositely-facing substantially planar radiation emitter surfaces.

17. A radiation source assembly, as recited in claim 14, said predetermined temperature being greater than about 900° C.

18. A radiation source assembly, as recited in claim 17, wherein said exterior ceramic layer and said holder each have a coefficient of thermal expansion, said coefficient of thermal expansion of said exterior ceramic layer differing by at least about 20 percent from said coefficient of thermal expansion of said holder.

19. A radiation source assembly, as recited in claim 14, said predetermined temperature being between about 900° C. and about 1200° C.

20. A radiation source assembly, as recited in claim 14, wherein said metalized portion comprises a brazeable material for providing a brazing interface on said exterior ceramic layer of said source element.

21. A radiation source assembly, as recited in claim 20, wherein said brazeable material comprises silver-copper brazing filler metal.

22. A radiation source assembly, as recited in claim 21, wherein said brazed interface layer comprises a material selected from the group consisting of tin-lead solder alloy and silver-copper brazing filler-metal.

23. A radiation source assembly, as recited in claim 20, wherein said holder is fabricated substantially from Zirconium Metal 702 or Kovar.

24. A radiation source assembly, as recited in claim 13, said holder having a substantially circular cross-section for providing a surface for mechanically and sealably interconnecting said radiation source assembly with the anesthetic gas monitoring device.

* * * * *